United States Patent [19]
Rossignol et al.

[11] Patent Number: 5,925,622
[45] Date of Patent: Jul. 20, 1999

[54] SYNTHESIS OF ARYL GLUCURONIDE OF 2-HYDROXY-N- (5-NITRO-2-THIAZOLYL) BENZAMIDE, AND PHARMACEUTICAL COMPOSITIONS COMPRISING SAME

[75] Inventors: Jean-François Rossignol, St. Petersburg; Marc S. Ayers, Tampa, both of Fla.

[73] Assignee: Romark Laboratories, L.C., Tampa, Fla.

[21] Appl. No.: 09/114,596

[22] Filed: Jul. 13, 1998

[51] Int. Cl.$^6$ ........................ A61K 31/70; A61K 31/425
[52] U.S. Cl. .............. 514/35; 514/371; 536/4.1; 536/17.6; 548/146; 548/192
[58] Field of Search .................. 514/23, 25, 35, 514/365, 370, 371; 536/4.1, 17.4, 17.6, 17.7, 17.9; 548/139, 140, 146, 163, 192

[56] References Cited

U.S. PATENT DOCUMENTS

| | | | |
|---|---|---|---|
| 3,496,187 | 2/1970 | Bruderlein et al. | 260/305 |
| 3,950,351 | 4/1976 | Rossignol et al. | 260/306.8 R |
| 5,578,621 | 11/1996 | Rossignol | 514/371 |
| 5,747,518 | 5/1998 | Yoshikawa et al. | 514/403 |
| 5,846,347 | 1/1999 | Hashiguchi et al. | 514/390 |
| 5,859,308 | 1/1999 | Rossignol | 514/371 |

FOREIGN PATENT DOCUMENTS

| | | |
|---|---|---|
| 6602878 | 9/1966 | Netherlands . |
| 460016 | 9/1968 | Switzerland . |
| 481938 | 11/1969 | Switzerland . |

OTHER PUBLICATIONS

Deshpande et al. "Aryl 5–Nitro–2–thiazolyl Sulfides, Sulfones and Esters as Potential Antibacterials", *J. Prak. Chem.*, vol. 316(2): 349–352, 1974.

Goodman & Gilman's The Pharmacological Basis of Therapeutics, Ninth Ed., pp. 11–14, 1996.

*Primary Examiner*—Howard C. Lee
*Attorney, Agent, or Firm*—Pendorf & Cutliff

[57] ABSTRACT

An aryl glucuronide of 2-hydroxy-N-(5-nitro-2-thiazolyl) benzamide, preferably an O-aryl glucuronide, as well as methods for the convenient synthesis of these aryl glucuronides, highly stable and low toxicity pharmaceutical composition containing these aryl glucuronides, and methods for use of these pharmaceutical compositions, for example, for treatment of inflammation, infections, etc.

6 Claims, No Drawings

SYNTHESIS OF ARYL GLUCURONIDE OF 2-HYDROXY-N-(5-NITRO-2-THIAZOLYL) BENZAMIDE, AND PHARMACEUTICAL COMPOSITIONS COMPRISING SAME

BACKGROUND OF THE INVENTION

1. Field of the Invention

The present invention concerns a method for the convenient synthesis of an aryl glucuronide of 2-hydroxy-N-(5-nitro-2-thiazolyl)benzamide, preferably an O-aryl glucuronide, or pharmaceutically acceptable salt thereof. The invention further relates to glucuronide pharmaceutical compositions characterized by high stability and low toxicity, and to methods for the use of these pharmaceutical compositions, for example, for treatment of inflammation, infections, etc.

2. Description of the Related Art

For a pharmaceutical compound to have true commercial value, it must satisfy every one of a long list of requirements.

One of the problems commonly encountered in the development of new pharmaceutical compounds is the stability of the compound in vivo. Numerous compounds have demonstrated promise in vitro, only to have an unsatisfactory short life when tested in vivo. This short life may be due to any of a number of reasons such as host organism immune response, enzymatic metabolism, etc.

On the other hand, numerous compounds which have been found to have satisfactory stability can not be utilized in practice because they lack the solubility required to be readily taken up by the host organism. This lack of solubility complicates the administration of the pharmaceutical compound.

Yet another criterion in the development of pharmaceutical compounds is target specificity. Compounds which are highly potent against a target organisms frequently tend also to have some amount of direct or indirect toxicity to the host organism. Pharmaceutical compounds with lower toxicity or fewer undesirable side effects are preferred.

Another criterion essential to pharmaceutical commercialization is the cost of synthesis of the pharmaceutical compound or composition. Complex organic syntheses may be cost prohibitive, particularly where less expensive alternative compounds are available. Further, as the synthesis protocol increases in complexity, so increases the susceptibility of the end product to inclusion of impurities, by-products or contaminants.

For all of the above reasons, new and useful pharmaceutical compounds satisfying all the requirements needed in the industry are rarely achieved. It is estimated that for every 2,000 drugs which show promise in vitro, only one ever reaches commercialization.

SUMMARY OF THE INVENTION

It is an object of the present invention to provide a new and useful pharmaceutical compound which has good pharmaceutical properties such as infection fighting and anti-inflammation properties, good solubility characteristics, good in vivo stability and low toxicity, and which can be synthesized by a relatively simple process.

It is further an object of the invention to provide a method for the convenient synthesis of an aryl glucuronide of 2-hydroxy-N-(5-nitro-2-thiazolyl)benzamide, preferably an O-aryl glucuronide, or pharmaceutically acceptable salt thereof.

It is yet a further object of the invention to provide pharmaceutical compositions comprising an aryl glucuronide of 2-hydroxy-N-(5-nitro-2-thiazolyl)benzamide, preferably an O-aryl glucuronide, or pharmaceutically acceptable salt thereof.

It is a further object of the invention to provide a method for treatment of viral, bacterial and parasitic infections as well as fever, pain and inflammation by administration to an infected organism an effective amount of a pharmaceutical agent comprising an aryl glucuronide of 2-hydroxy-N-(5-nitro-2-thiazolyl)benzamide, preferably an O-aryl glucuronide, or pharmaceutically acceptable salt thereof.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other pharmaceutical compositions and methods for treatment for carrying out the same purposes of the present invention. It should also be realized by those skilled in the art that such equivalent formulations and methods do not depart from the spirit and scope of the invention as set forth in the appended claims.

DETAILED DESCRIPTION OF THE INVENTION

After extensive experimentation, the present inventors discovered pharmaceutical compounds which have good therapeutic properties, which are low in toxicity, which have good in vivo stability, good solubility characteristics, and further, they have discovered a process by which these compound could be manufactured economically, as described below.

The present invention concerns a novel compound which may be an ortho-, meta-, or para-isomer of an aryl glucuronide of 2-hydroxy-N-(5-nitro-2-thiazolyl)benzamide, and having the following formula:

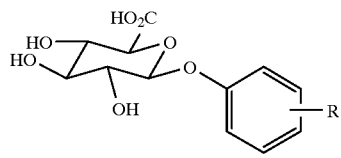

wherein

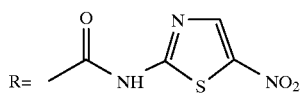

Particularly preferred is the ortho-isomer of the aryl glucuronide, being represented by the following formula (1):

(1)

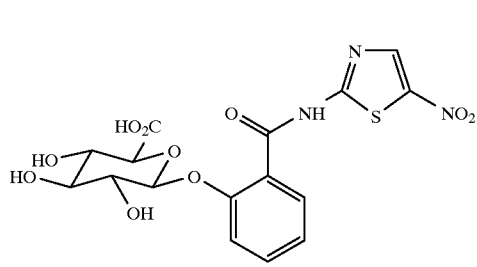

The present invention further concerns pharmaceutical compositions containing as active agent compounds of this formula (1) and/or the meta- and para-isomers thereof, and processes for the synthesis of these compounds.

In order to give an overview of the synthesis, a brief explanation will be given first, from which the reagents, catalysts, and conditions will be omitted.

Basically, the process may begin with salicylic acid. Desiring to react the hydroxy salicylic acid with glucuronic acid, it was surprisingly found possible to do this by first blocking the acid position of the salicylic acid by making this into an ester, so that it would not interfere with the hydroxy substituent. One thus obtains for example a benzyl salicylate (2), the benzyl ester being chosen to allow selective deprotection later.

(2)

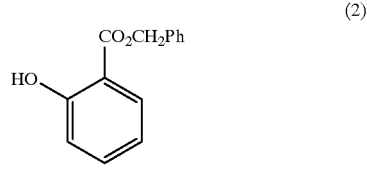

Next, as step (i) of a scheme 1 discussed in greater detail below, one takes, e.g., an alpha bromide derivative of glucuronate (3)

(3)

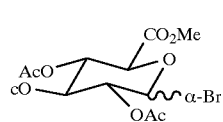

and reacts this with the above-discussed ester of salicylic acid (2). As shown in scheme 1, one obtains an ester represented by formula (4). The subsequent synthesis can be shown in Scheme 1 as follows:

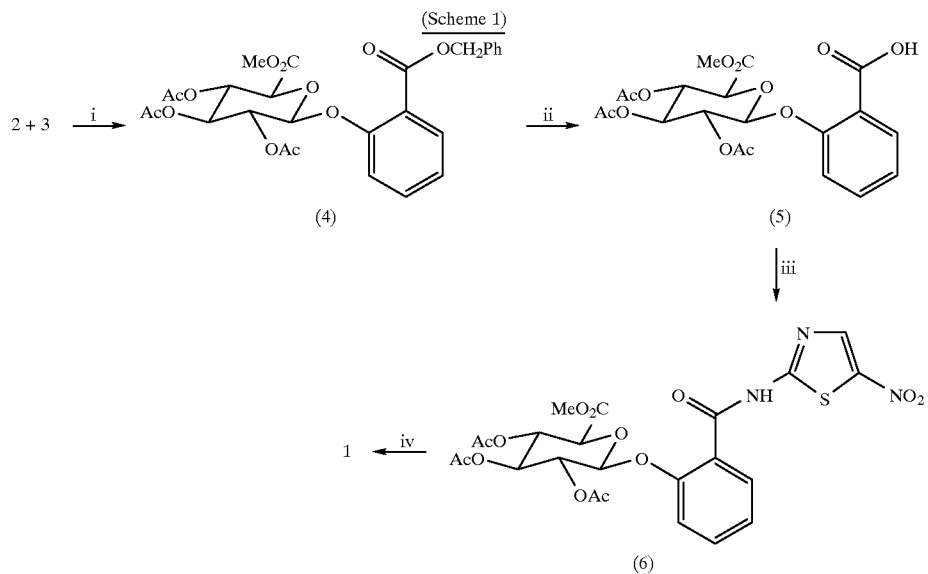

Step (ii) involves a hydrolysis of the ester (4) to return to an acid (5).

Step (iii) reacts compound (5) with 2-amino-5-nitrothiazole.

In step (iv) esters are cleaved without affecting the amide link using, e.g., aq. NaOH, such that after acidification to pH 6 the sodium salt of glucuronide (1) is produced.

For illustration purposes Scheme 1 is shown to produce the ortho-glucuronide, but the same processes can be used to produce meta-, or para-isomers by the simple substitution of the salicylic acid with the appropriate meta- or para-isomer.

It is surprising that the glucuronide derivative of salicylic acid would be a molecule strong enough to be able to react with the 2-amino-5-nitrothiazole without degradation. This further shows the strength of the final structure, which translates into in vivo stability.

In accordance with the present invention, it was surprisingly discovered that a procedure for the glucuronidation of methyl salicylate (C. D. Lumsford and R. S. Murphy, *J. Org. Chem.*, 1956, 21, 580) could be very satisfactorily applied to produce the more sophisticated O-aryl glucuronide (1) in accordance with scheme 1.

EXAMPLE 1

Synthesis of O-aryl glucuronide (1)

Reagents and conditions: i) $Ag_2O$, isoquinoline, 0–20° C.; ii) cyclohexene, Pd-C, $Pr^iOH$, $\Delta$; iii) $EtN=C=N(CH_2)_3N^+Me_2$ $Cl^-$, 1-hydroxybenzotriazole, 4-dimethylaminopyridine, 2-amino-5-nitrothiazole, DMF; iv) NaOH, MeOH aq., 0–20° C. then pH 6.

Step (i)

Koenigs-Knorr coupling of (2) with (3) in step (i) was carried out as follows: Silver(I) oxide (2.12 g, 0.91 mmol) was added in portions to a mixture of bromosugar (3) (3.30 g, 8.31 mmol) and benzyl salicylate (2) (3.78 g, 16.6 mmol) in isoquinoline (4.6 g) which was stirred at 0° C., giving a thick slurry. On warming to 20° C. the mixture was diluted with ether and filtered through Celite, washing the precipitate with ether, then the combined filtrate and washings were washed with 2.5 mol $dm^{-3}$ HCl (2×), satd. aq. $NaHCO_3$ and water followed by evaporation to an orange oil which was washed with hexane (2×), decanting the mother liquors. Chromatography on silica, eluting with 20 to 50% EtOAc in hexane in 10% steps, afforded on pooling and evaporation of appropriate fractions the product (4) as a foam (2.75 g, 61%) (Found: m/z, 562.1933. $C_{27}H_{32}NO_{12}$ requires $MNH_4^+$, 562.1924); max. $(CHCl_3)/cm^{-1}$ 1 750 (vs), 1 610, 1 590 (sh) and 1 490; $\delta$ $(CDCl_3)$ 2.09 (9 H, s, 3×$CH_3CO$), 3.77 (3 H, s, $CH_3O$),4.21 (1 H, d, 5-H), 5.20 (1 H, m, 1-H), 5.30–5.40 (3 H, m, 2-H+3-H+4-H), 5.37 (2 H, s, $PhCH_2$ O), 7.10–7.25 (2 H, m, ArH) 7.35–7.55 (6 H, m, ArH) and 7.81 (1 H, dd, ArH); m/z (C. I., $NH_3$) 562 ($MNH_4^+$, 65%).

Thus, using isoquinoline as both solvent and base, the fully protected ester (4), methyl 1-[(2-benzyloxycarbonyl) phenyl]-2,3,4-tri-O-acetyl-β-D-glucopyranuronate, was produced in 61% yield after chromatography.

Step (ii)

Selective removal of the benzyl ester was then effected using catalytic transfer hydrogenation to give acid (5), methyl 1-(2-carboxyphenyl)-2,3,4-tri-O-acetyl-β-D-glucopyranuronate, in 80% yield as follows.

10% Palladium on carbon (0.3 g) was added to a solution of ester (5) (2.71 g, 4.98 mmol) in isopropanol (75 $cm^3$) and cyclohexene (5 $cm^3$) and the mixture was stirred and heated at gentle reflux for 0.5 h. The precipitate was filtered off on Celite and washed with further isopropanol, then the combined filtrate and washings were evaporated to a foam which was dissolved in half-satd. aq. $NaHCO_3$ (25 $cm^3$) and washed with ether (2×). The aqueous phase was cautiously acidified with 10% aq. citric acid until precipitation was complete, then the product was extracted with ether (2×25 $cm^3$) and the combined extracts evaporated to give the acid (5) as a colorless foam (1.84 g, 80%) (Found: C, 52.4; H, 4.9; m/z, 472.1465. $C_{20}H_{22}O_{12}$ requires C, 52.85; H, 4.8%; $MNH_4^+$, 472.1455); max. $(Nujol)/cm^{-1}$ 3 700-2 500 (br), 1 760 (br, s), 1 610 (m) and 1 495; $\delta$(220 MHz, $CDCl_3$) 2.00–2.10 (9 H, 3 s, 3×$CH_3CO$), 3.73 (3 H, s, $CH_3O$), 4.34 (1 H, d, 5-H), 5.35–5.45 (4 H, m, 1-H to 4-H), 7.28 (2 H, m ArH), 7.62 (1 H, t, ArH) and 8.11 (1 H, d, ArH); m/z (C. I., $NH_3$) 100%.

Step (iii)

The condensation of (5) with 2-amino-5-nitrothiazole in step (iii) was best performed using the water-soluble carbodiimide method shown to facilitate removal of by-products; 4-dimethylaminopyridine was added to achieve a good reaction rate.

1-(3-dimethylaminopropyl)-3-ethylcarbodiimide hydrochloride (0.81 g, 4.24 mmol) was added to a suspension of acid (5) (1.75 g, 3.85 mmol), 4-N, N-dimethylaminopyridine (0.5 g, 4.10 mmol), 1-hydroxybenzotriazole monohydrate (0.65 g, 4.25 mmol) and 2-amino-5-nitrothiazole (0.615 g, 4.24 mmol) which was stirred in DMF (25 $cm^3$) at 0° C. The reaction was allowed to regain ambient temperature, giving a brown solution, then after 2 h it was stored at 0° C. for 16 h when TLC (10% methanol-chloroform) indicated complete reaction. The solution was concentrated to near dryness, then partitioned between 5% aq. citric acid (50 $cm^3$) and DCM (2×50 $cm^3$). The combined organic extracts were washed with 5% aq. citric acid, satd. aq. $NaHCO_3$ (2×) and water (2×), backwashing each time with a little DCM and breaking emulsions by adding brine. Evaporation gave a brown solid (2.63 g) which was dissolved in 10% methanol-DCM and chromatographed on silica, eluting with DCM, then with 2–7% methanol-DCM in steps. Appropriate fractions were pooled and evaporated to a sticky solid which on trituration with ether deposited the product (6) methyl 1-[[2- N-(5-nitrothiazolyl)carboxamido]phenyl]-2,3,4-tri-O-acetyl-β-D-glucopyranuronate, as a flaky yellow solid (1.51 g, 67%), m. p. 262–264° C. (Kofler block, from DCM-methanol-ether) (Found: C, 47.5; H, 4.15; N, 7.15. $C_{23}H_{23}N_3O_{13}S$ requires C, 47.5; H, 4.0; N, 7.2%); max. $(Nujol)/cm^{-1}$ 3 350 (sharp), 1 750, 1 665, 1 625 (w), 1 605 (m), 1 530 and 1 350; $\delta$ $[(CD_3)_2SO]$ 1.94, 1.98, 2.05 (9 H, 3 s, 3×$CH_3CO$), 3.68 (3 H, s, $CH_3O$), 4.80 (1 H, d, 5-H), 5.05 (2 H, t) and 5.48 (1 H, t, 2-H+3-H+4-H), 5.67 (1 H, d, 1-H), 7.20–7.30 (2 H, m, ArH), 7.55–7.70 (2 H, m, ArH) 8.71 (1 H, s, 4"-H) and 13.39 (1 H, br s, NH); m/z (C. I., $NH_3$) 582 ($MH^+$, 100%).

Step (iv)

Finally the esters were cleaved without affecting the amide link using aq. NaOH, and after acidification to pH 6 the sodium salt of glucuronide (1), 1-[[2-N-(5-nitrothiazolyl)carboxamido]phenyl]-β-D-glucopyranosiduronic acid, was obtained as a solid in 80% yield.

A 2.5 mol $dm^{-3}$ NaOH solution (5 $cm^3$) was added in one portion to a stirred suspension of the ester (6) (1.45 g, 2.50 mmol) in methanol (17.5 $cm^3$) at 0° C. On warming to 20° C. over 1 h, a yellow solution resulted which was acidified to pH 6.9 with acetic acid, followed by evaporation to dryness. The residue was triturated with aq. ethanol, 1:4 (20 $cm^3$); after cooling to complete precipitation, the yellow solid was filtered to give the sodium salt of the product (1) (1.03 g, 89%), m. p. >200° C. (dec.) from aq. ethanol (Found: m/z, 464.0367. $C_{16}H_{15}N_3O_{10}SNa$ requires $MH^+$, 464.0376); max. $(Nujol)/cm^{-1}$ 3 700–2 500 (br), 3 540, 3 260, 3 100 (w), 1 645 (sh), 1 620, 1 600, 1 535 and 1 350; $\delta$ $[(CD_3)_2SO+D_2O]$ 3.53 (2 H, m) and 3.67 (1 H, t, 2-H+ 3-H+4-H), 3.83 (1 H, d, 5-H), 5.14 (1 H, d, J 8 Hz, 1-H), 7.16 (1 H, t, ArH), 7.29 (1 H, d, ArH), 7.54 (1 H, dt, ArH), 7.74 (1 H, dd, ArH) and 8.38 (1 H, s, 4"-H); m/z (F. A. B. +ve ion, glycerol) 442 ($MH^+$, free acid), 464 ($MH^+$) and 486 ($MNa^+$).

High-performance liquid chromatographic analysis of the product ($C_{18}$ λ-bondapak reverse-phase column, aq. acetonitrile eluent) showed an area purity of 99.25%.

Biological Data

Antibacterial screening was performed using either an agar dilution technique in a Wilkens Chalgren medium containing 10% blood at an inoculum of $10^9$ colony forming units (CFU)/cm$^3$, for the anaerobic bacteria, or in a Mueller Hinton agar medium at an inoculum of $10^6$ CFU/cm$^3$ in Mueller Hinton broth for the aerobic bacteria.

The antibacterial activity of glucuronide (1) was tested and activity against anaerobic bacteria was observed.

More specifically, minimum inhibitory concentrations (MICs) in the range 1–10 µg/ml were observed against *Helicobacter pylori*. Against *Sarcocystis neurona*, (1) showed MICs of 40 µg/ml. Also observed was good in vivo stability of the compound, good solubility, and good tolerance, i.e., low toxicity. A further interesting effect observed was an anti-inflammatory property.

Pharmaceutical Preparations

Due to good stability and solubility, the aryl glucuronide of 2-hydroxy-N-(5-nitro-2-thiazolyl)benzamide is preferably administered in the form of a liquid, i.e., intravenously, but may be administered orally in solid or liquid forms.

The dosage of the aryl glucuronide of 2-hydroxy-N-(5-nitro-2-thiazolyl)benzamide to be administered depends upon the target bacteria or microorganism, with dosages ranging from 1–10 µg/ml. The active agent should be administered to a warm blooded mammal in need of treatment in a dosage of from 2–200 mg/kg/day, preferably 5–150 mg/kg/day, as needed, usually over a period of one to three weeks.

Techniques for preparation of, and preferred examples of, solid and liquid dosage forms of a related pharmaceutical composition are well known and need not be discussed herein in detail.

Such pharmaceutical compositions, either as solid or liquid dosage forms or as pastes or ointments, can optionally contain additional active agents such as antibiotics, antiviral agents or proton pump inhibitors.

The compositions can contain excipients known as such for the purpose of preparing forms suitable for oral administration. The efficacy and the safety of the pharmaceutical compositions disclosed hereabove were excellent in animals and in humans.

With respect to the above description then, it is to be realized that the optimum formulations and methods of the invention are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Now that the invention has been described,
What is claimed is:

1. 1-[[2-N-(5-nitrothiazolyl)carboxamido]phenyl]-β-D-glucopyranosiduronic acid.

2. An aryl glucuronide of 2-hydroxy-N-(5-nitro-2-thiazolyl)benzamide represented by the following formula:

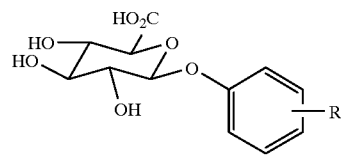

wherein

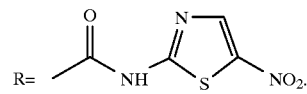

3. A pharmaceutical composition comprising, as active agent, 1-[[2-N-(5-nitrothiazolyl)carboxamido]phenyl]-β-D-glucopyranosiduronic acid.

4. A pharmaceutical composition comprising, as active agent, an aryl glucuronide of 2-hydroxy-N-(5-nitro-2-thiazolyl)benzamide represented by the following formula:

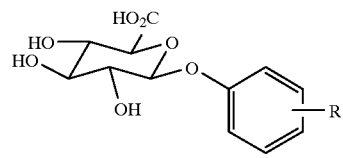

wherein

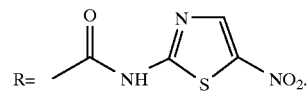

5. A method for producing the aryl glucuronide of 2-hydroxy-N-(5-nitro-2-thiazolyl)benzamide, the method comprising:

(i) reacting an ester of salicylic acid with an alpha halogenated derivative of glucuronate to produce methyl 1-[(2-benzyloxycarbonyl)phenyl]-2,3,4-tri-O-acetyl-β-D-glucopyranuronate;

(ii) effecting hydrolysis methyl 1-[(2-benzyloxycarbonyl)phenyl]-2,3,4-tri-O-acetyl-β-D-glucopyranuronate to form methyl 1-(2-carboxyphenyl)-2,3,4-tri-O-acetyl-β-D-glucopyranuronate;

(iii) reacting the product of step (ii) with 2-amino-5-nitrothiazole to produce methyl 1-[[2-N-(5-nitrothiazolyl)carboxamido]phenyl]-2,3,4-tri-O-acetyl-β-D-glucopyranuronate, (iv) cleaving the glucuronide esters from the product of step (iii) followed by acidification to produce 1-[[2-N-(5-nitrothiazolyl)carboxamido]phenyl]-β-D-glucopyranosiduronic acid.

6. A method for producing the aryl glucuronide of 2-hydroxy-N-(5-nitro-2-thiazolyl)benzamide, the method comprising:

(a) providing an ester of a salicylic acid;
(b) reacting said ester of the salicylic acid with an alpha-halogenated glucuronate;
(c) effecting hydrolysis of the ester product of step (b) to form an acid;
(d) reacting the product of step (c) with a 2-amino-5-nitrothiazole,
(e) cleaving the esters from the product of step (d) in alkaline hydroxide without affecting the amide link, and
(f) subjecting the product of step (e) to acidification.

* * * * *